United States Patent [19]

Frazer

[11] 4,096,341
[45] Jun. 20, 1978

[54] THERMALLY STABLE, RIGID DIBASIC ACIDS

[75] Inventor: August Henry Frazer, Wilmington, Del.

[73] Assignee: E. I. Du Pont de Nemours and Company, Wilmington, Del.

[21] Appl. No.: 828,143

[22] Filed: Aug. 26, 1977

Related U.S. Application Data

[62] Division of Ser. No. 751,086, Dec. 16, 1976.

[51] Int. Cl.² .............................................. C07C 69/76
[52] U.S. Cl. ........................................ 560/85; 560/89
[58] Field of Search .................................. 560/85, 89

[56] References Cited

U.S. PATENT DOCUMENTS

| | | | |
|---|---|---|---|
| 3,440,221 | 4/1969 | Quisenberry | 260/75 R |
| 3,477,989 | 11/1969 | Zorn et al. | 260/47 C |
| 3,511,809 | 5/1970 | Hogsed et al. | 260/47 C |
| 3,522,217 | 7/1970 | Weimar | 260/75 R |

Primary Examiner—Lucille M. Phynes

[57] ABSTRACT

Thermally stable, rigid dibasic acids of the formula

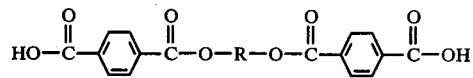

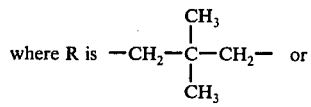

or

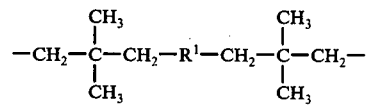

wherein $R^1$ is arylene or substituted arylene, are used to prepare thermally stable, rigid polyesters of the formula

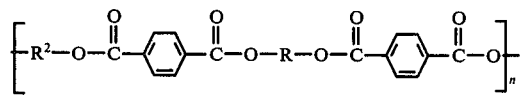

where $R^2$ is arylene or substituted arylene, and $n$ is at least 10.

4 Claims, No Drawings

THERMALLY STABLE, RIGID DIBASIC ACIDS

CROSS-REFERENCE TO RELATED APPLICATION

This is a division of my copending application Ser. No. 751,086 filed Dec. 16, 1976.

BACKGROUND OF THE INVENTION

(1) Field of the Invention

This invention is concerned with thermally stable, high tenacity, high modulus polyesters prepared from aromatic dihydroxy compounds and thermally stable, rigid diacids containing no aliphatic beta-hydrogen atoms.

(2) Description of the Prior Art

Polyester fibers such as those spun from polyethylene terephthalate have found wide commercial acceptance. These fibers, however, generally have limited thermal stability. A major pathway for thermal decomposition of known aliphatic-aromatic polyesters is thermal elimination at the site of aliphatic beta-hydrogens.

Polyesters having improved thermal stability have been prepared from terephthalic acid and neopentyl glycol. These polymers do not contain aliphatic beta-hydrogens. Such polyesters are described in British Pat. No. 828,922, French Pat. No. 1,392,313 and U.S. Pat. Nos. 3,194,794 and 3,498,952. These polyesters, however, are amorphous and thus have limited strength as fibers.

It would be desirable to provide new polyesters of superior thermal stability which could be melt spun into fibers characterized by high tenacity and high modulus. Such fibers would be useful, for example, as tire cords.

SUMMARY OF THE INVENTION

There have now been discovered thermally stable, rigid dibasic acids of the formula

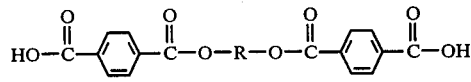

where R is —CH$_2$—C(CH$_3$)$_2$—CH$_2$— or

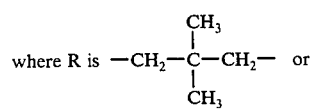

where R$^1$ is an arylene selected from the group consisting of 1,4-phenylenes, 4,4'-biphenylenes and 2,6-naphthylenes, said arylene being unsubstituted or substituted with halo, lower alkyl or phenyl.

These dibasic acids are useful in the preparation of thermally stable, rigid, ordered polyesters of the formula

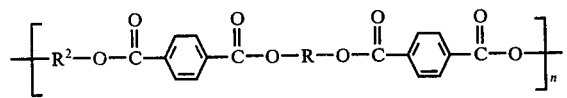

where R is —CH$_2$—C(CH$_3$)$_2$—CH$_2$— or

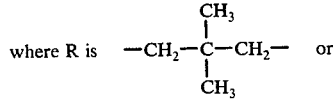

where R$^1$ is as defined above,
R$^2$ is defined the same as R$^1$, specific embodiments of R$^1$ and R$^2$ being alike or different, and
n is at least about 10.

The term "rigid" is used to denote the presence of a sufficient quantity of aromatic rings in the backbone of the molecule to provide stiffness. The term "halo" is intended to include chloro, bromo, fluoro and iodo. The term "lower alkyl" is intended to include alkyls of 1 to 6 carbons. In the definition of R$^1$ the substituted phenylene may have 1 to 4 of the specified substituents, the substituted biphenylene may have 1 to 8 of these substituents, and the substituted naphthylene may have 1 to 6 of these substituents.

DESCRIPTION OF THE PREFERRED EMBODIMENT

The thermally stable, rigid dibasic acids of this invention are of the formula

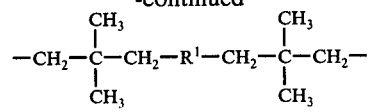

where R is as defined above. These dibasic acids are prepared by reacting neopentyl glycol, or a rigid diol of the formula

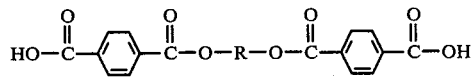

where R$^1$ is arylene or substituted arylene as specified above, with the half acid chloride of terephthalic acid.

The rigid diols are prepared by reacting a lower alkyl isobutyrate such as methyl isobutyrate with an α,α'-dibromo aromatic compound such as α,α'-dibromo-p-xylene in the presence of the reaction product of a lower alkyllithium such as n-butyllithium with a hindered secondary amine such as diisopropylamine to form a 1,4-bis(2-carbomethoxy-2-methylpropyl)benzene in accordance with the equation:

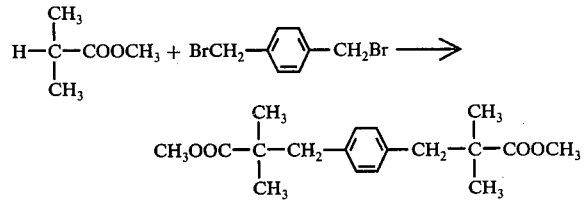

This product is then reduced with lithium aluminum hydride to form the rigid diol in accordance with the equation:

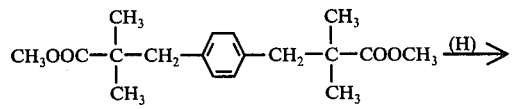

-continued

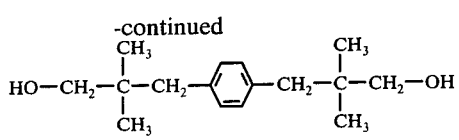

Rigid diols having different arylene groups are obtained by substituting a different α,α'-dibromo aromatic compound for α,α'-dibromo-p-xylene. Suitable α,α'-dibromo aromatic compounds include α,α'-dibromo-p-xylene
α,α'-dibromo-p,p'-bitolyl
2,6-bis(bromomethyl)naphthylene
α,α'-dibromo-2-chloro-p-xylene
α,α'-dibromo-2-methyl-p-xylene
α,α'-dibromo-2-ethyl-p-xylene
α,α',2-tribromo-p-xylene
3,6-bis(chloromethyl)durene
2,5-bis(bromomethyl)biphenyl
4,4'-bis(bromomethyl)-3,3'-difluorobiphenyl
3,3'-dichloro-4,4'-bis(bromomethyl)biphenyl
1,5-dichloro-2,6-bis(bromomethyl)naphthalene
1-chloro-2,6-bis(bromomethyl)naphthalene
and the like.

The thermally stable, rigid, ordered polyesters of this invention are of the formula

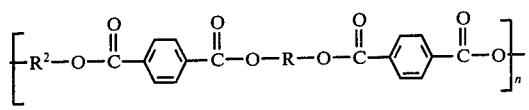

where R, R² and n are as defined above. These polyesters are prepared by reacting a rigid dibasic acid of this invention with an aromatic dihydroxy compound or diester of the formula

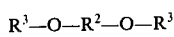

in which R² is as defined above, and R³ is hydrogen or

where R⁴ is a hydrocarbyl group of 1 to 10 carbon atoms selected from the group consisting of alkyl, aryl, aralkyl and alkaryl.

Suitable aromatic dihydroxy compounds for preparing the polyesters of this invention are known compounds which include:

hydroquinone
chlorohydroquinone
methylhydroquinone
4,4'-dihydroxybiphenyl
3-chloro-4,4'-dihydroxybiphenyl
3,3'-dichloro-4,4'-dihydroxybiphenyl
4,4'-dihydroxy-2-methylbiphenyl
4,4'-dihydroxy-3,3'-dimethylbiphenyl
2,6-naphthalenediol
1,5-dichloro-2,6-naphthalenediol
tetrabromohydroquinone
tetrachlorohydroquinone
tetrafluorohydroquinone
tetraiodohydroquinone
tetramethylhydroquinone
butylhydroquinone
2-ethyl-3,5-dimethylhydroquinone
2,5-di-tertiarybutylhydroquinone
2,5-diphenylhydroquinone
3,5,3',5'-tetrabromo-4,4'-dihydroxybiphenyl
3,5,3',5'-tetrachloro-4,4'-dihydroxybiphenyl
4,4'-dihydroxy-3,5,3',5'-tetramethylbiphenyl
4,4'-dihydroxy-3,3'-dimethyl-5,5'-dipropylbiphenyl
octachloro-4,4'-dihydroxybiphenyl
octafluoro-4,4'-dihydroxybiphenyl
4,4'-dihydroxyoctamethylbiphenyl
and the like.

The aromatic dihydroxy diesters in which R³ is

are prepared by reacting the corresponding aromatic dihydroxy compound in which R³ is hydrogen with a carboxylic acid anhydride by known esterification procedures. Suitable anhydrides for preparing the corresponding diesters include acetic, propionic, n-butyric, benzoic, phenylacetic, p-toluic, and α-naphthoic anhydrides, and the like.

The polyesters of this invention are prepared by melt polymerization, that is, heating the rigid dibasic acid and the aromatic dihydroxy compound or diester at a temperature above the melting point of the ingredients. A diester of the aromatic dihydroxy compound is generally used rather than the dihydroxy compound itself because of the lower melting point of the diester. When a faster reaction is desired, the dihydroxy compound itself can be used.

The ordered polyesters of this invention are characterized by superior thermal stability, high tenacity and high stiffness modulus. A contributing factor in the superior thermal stability is the absence of β-hydrogens in the aliphatic portions of the molecule. These ordered polyesters have superior stability in high temperature melt polymerizations, in high temperature melt spinning, and in extrusion operations.

The chain stiffness or rigidity imparted by the aromatic segments in the polymers contributes to the high tenacity and high stiffness modulus of fibers spun from the polymers. Many of these polymers yield oriented fibers directly from melt spinning. A particularly preferred group of the polymers of this invention are those having glass transition temperatures above 150° C. Fibers of these polymers have the practical advantages of high strength and high modulus at elevated temperatures. The polyesters of this invention are especially useful for preparing tire cords.

EXAMPLES OF THE INVENTION

The following examples illustrate the preparation of the thermally stable, rigid dibasic acids of this invention and their use in the preparation of the thermally stable, rigid, ordered polyesters of this invention. In the examples the following tests and designations were employed.

Polymer melt temperature (PMT) is that temperature at which a fresh polymer sample leaves a wet molten trail when stroked with moderate pressure across a clean, heated metal surface. A temperature-gradient bar covering the range of 50°–400° C was used for this determination (Beaman and Cramer, J. Polymer Sci., XXI, page 227).

Inherent viscosity was determined at 0.5% concentration and 30° C in a 40/60 weight mixture of 1,2,2,2-tetrachloroethane and phenol.

The standard fiber test designation T/E/Mi refers to tensile strength in grams per denier, elongation in percent, and initial modulus in grams per denier.

Orientation angle was determined by the method described by Kwolek in U.S. Pat. No. 3,671,542 at Column 20, lines 8–41.

EXAMPLE 1

Part A

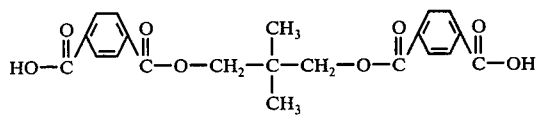

A mechanically stirred mixture of 15.6 g (0.15 M) of 2,2-dimethyl-1,3-propanediol, 92.25 g (0.5 M) of 4-carboxybenzoyl chloride and 500 ml of pyridine was refluxed under a nitrogen atmosphere. The resulting mixture was concentrated to dryness under reduced pressure, dispersed in 500 ml of distilled water, and acidified to pH 1 with concentrated hydrochloric acid. The precipitate was filtered off, washed three times with distilled water, and dried overnight at 100° C in a vacuum oven. The product was extracted for 5 days with 2 liters of hot benzene. The extract, on cooling, yielded 48.2 g of 4,4'-[(2,2-dimethyl-1,3-propanediyl)bis(oxycarbonyl)]bis(benzoic acid) melting at 287°–288° C. The infrared spectrum was consistent with the proposed structure and the compound was found to contain 5.13 meq of $CO_2H$/g which corresponded to a molecular weight of 390 for the diacid.

Part B

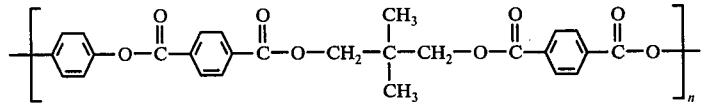

To a glass reactor with a nitrogen bleed and sidearm was added 1.950 g (0.005 M) of the diacid from Part A and 1.028 g (0.0053 M) of hydroquinone diacetate. The resulting mixture under a nitrogen atmosphere was heated for 18 hr at 242° C, for 2 hr at 275° C, and for 2 hr at 305° C, followed by 2 hr at 305° C at 0.01 mm. The resulting poly[oxycarbonyl(1,4-phenylene)carbonyloxy(2,2-dimethyl-1,3-propanediyl)oxycarbonyl(1,4-phenylene)carbonyloxy(1,4-phenylene)] had a PMT >400° C and was insoluble in a 40/60 weight mixture of 1,1,2,2-tetrachloroethane and phenol.

EXAMPLE 2

Part A

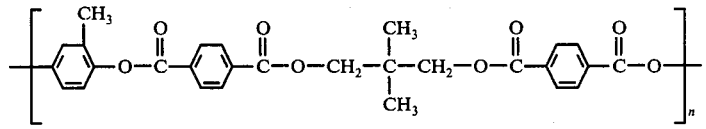

To a glass reactor with a nitrogen bleed and sidearm was added 21.84 g (0.04 M) of the diacid from Example 1, Part A, and 8.53 g (0.041 M) of methylhydroquinone diacetate. The resulting mixture under a nitrogen atmosphere was heated for 36 hours at 242° C, and for 6 hours at 275° C, followed by 3 hours at 275° C at less than 0.05 mm Hg pressure. The resulting poly[oxycarbonyl(1,4-phenylene)carbonyloxy(2,2-dimethyl-1,3-propanediyl)oxycarbonyl(1,4-phenylene)carbonyloxy(2-methyl-1,4-phenylene)] had a PMT of approximately 400° C, an inherent viscosity of 0.75, and showed low crystallinity by X-ray diffraction.

Part B

Polymer from Part A was spun at a spinneret temperature of 370° C and the fiber was wound up at 250 yd/min. The fiber could not be drawn and after being heated at 250° C for 18 hours under a nitrogen atmosphere under restrained conditions, had an orientation angle of 21°, was of medium crystallinity, had a T/E/Mi at room temperature of 7.2/2.1/310 and a T/E/Mi at 150° C of 5.8/2/248.

EXAMPLE 3

Part A

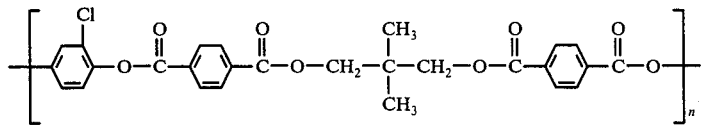

To a glass reactor with a nitrogen bleed and sidearm was added 20.00 g (0.05 M) of the diacid from Example 1, Part A, and 11.62 g (0.0513 M) of chlorohydroquinone diacetate. The resulting mixture was heated as in Example 2, Part A. The resulting poly[oxycarbonyl(1,4-phenylene)carbonyloxy(2,2-dimethyl-1,3-propanediyl)oxycarbonyl(1,4-phenylene)carbonyloxy(2-chloro-1,4-phenylene)] had a PMT of approximately 400° C, an inherent viscosity of 0.62, and showed low crystallinity by X-ray diffraction.

Part B

Polymer from Part A was spun at a spinneret temperature of 375° C and the fiber was wound up at 200 yd/min. The fiber could not be drawn and after being heated at 250° C for 18 hours under a nitrogen atmosphere, had an orientation angle of 22°, was of medium crystallinity, had a T/E/Mi at room temperature of 3.6/2.1/260 and a T/E/Mi at 150° C of 2.8/2/208.

EXAMPLE 4

Part A

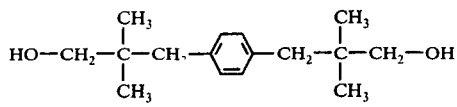

To 1 liter of dry tetrahydrofuran was added 52 g of diisopropylamine. The mixture was cooled to −78° C and 325 ml of 1.6 M n-butyllithium in hexane was added. After 1 hr of stirring 52 g of methyl isobutyrate was added dropwise followed by stirring for another 30 minutes. Then 63 g of α,α'-dibromo-p-xylene was slowly added. The reaction mixture was stirred overnight and brought to room temperature. The mixture was filtered and solvent was removed from the filtrate by evaporation. The residue was recrystallized from methanol to obtain 63 g of 1,4-bis(2-carbomethoxy-2-methylpropyl)-benzene, mp 74°–76° C.

To 500 ml of dry tetrahydrofuran was added 11.4 g of lithium aluminum hydride and 60 g of 1,4-bis(2-carbomethoxy-2-methylpropyl)benzene. The mixture was stirred overnight at room temperature. To the thick reaction mixture was added 300 ml of ethyl acetate, 30 ml of saturated aqueous NH$_4$Cl and 5 ml of concentrated HCl. The mixture was stirred and filtered. Solvent was evaporated from the filtrate and the residue was recrystallized from benzene to obtain 20 g of 1,4-bis(3-hydroxy-2,2-dimethylpropyl)benzene. The solid from the above filtration was slurried with 50 ml of H$_2$O, 20 ml of concentrated HCl and 150 ml of benzene and heated at reflux for 1 hour. The benzene layer was then separated, dried over MgSO$_4$ at 80° C, filtered hot and then cooled to precipitate an additional 10 g of 1,4-bis(3-hydroxy-2,2-dimethylpropyl)-benzene, mp 104°–105° C.

Part B

A mechanically stirred mixture of 17.5 g (0.07 M) of 1,4-bis(3-hydroxy-2,2-dimethylpropyl)benzene, 42.4 g (0.23 M) of 4-carboxybenzoyl chloride and 500 ml of pyridine was refluxed under a nitrogen atmosphere. The resulting mixture was concentrated to dryness under reduced pressure, dispersed in 500 ml of distilled water, and acidified to pH 1 with concentrated hydrochloric acid. The precipitate was filtered off, washed three times with distilled water, and dried overnight at 100° C in a vacuum oven. The product was extracted for 5 days with 2 liters of hot benzene. The extract, on cooling yielded 30.4 g of 4,4'-[1,4-phenylenebis(2,2-dimethyl-3,1-propanediyl)(oxycarbonyl)]bis(benzoic acid) melting at 296°–297° C. The infrared spectrum was consistent with the proposed sturcture and the compound was found to contain 3.92 meq of CO$_2$H/g corresponding to a molecular weight of 510 for the diacid.

Part C

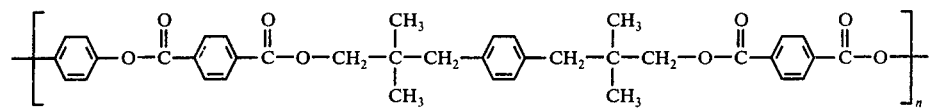

To a glass reactor with a nitrogen bleed and a sidearm, was added 2.550 g (0.005 M) of the diacid from Part B above and 1.028 g (0.0053 M) of hydroquinone diacetate. The resulting mixture was heated for 18 hours at 242° C, for 2 hours at 275° C, and for 2 hours at 305° C, followed by 2 hours at 305° C at 0.01 mm. The resulting poly[oxycarbonyl(1,4-phenylene)carbonyloxy(2,2-dimethyl-1,3-propanediyl)(1,4-phenylene)(2,2-dimethyl-1,3-propanediyl)oxycarbonyl(1,4-phenylene)carbonyloxy(1,4-phenylene)] had a PMT >400° C and was insoluble in a 40/60 weight mixture of 1,1,2,2-tetrachloroethane and phenol.

Part D

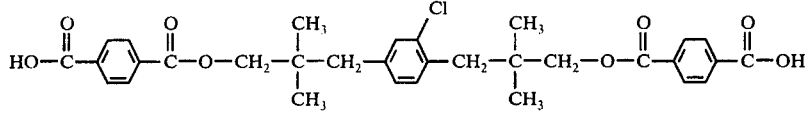

When α,α'-dibromo-2-chloro-p-xylene is substituted for α,α'-dibromo-p-xylene in the procedure of Example 4, Part A, the diol obtained is 1,4-bis(3-hydroxy-2,2-dimethylproyl)2-chlorobenzene, and the dibasic acid obtained in the procedure of Part B is 4,4'-[2-chloro-1,4-phenylenebis(2,2-dimethyl-3,1-propanediyl) (oxycarbonyl)]bis(benzoic acid).

Part E

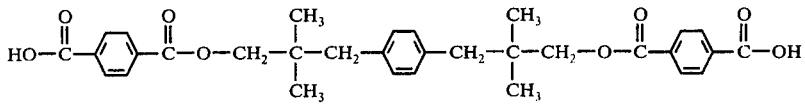

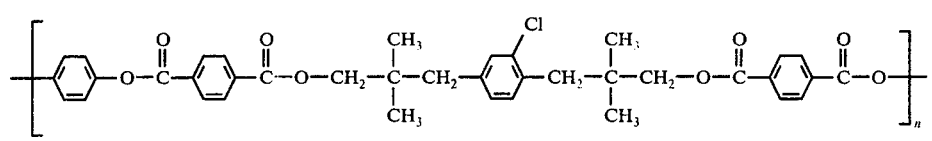

When the dibasic acid obtained in Part D is used in the procedure of Example 4, Part C, the polymer obtained is poly[oxycarbonyl(1,4-phenylene)carbonyloxy(2,2-dimethyl-1,3-propanediyl)(2-chloro-1,4- zene, and the dibasic acid obtained in the procedure of Part B is 4,4'-[2-methyl-1,4-phenylenebis(2,2-dimethyl-3,1-propanediyl)(oxycarbonyl)]bis(benzoic acid).

Part I

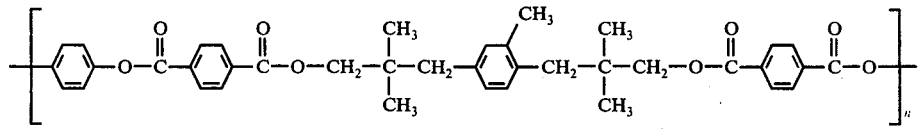

phenylene)(2,2-dimethyl-1,3-propanediyl)oxycarbonyl(1,4-phenylene)carbonyloxy(1,4-phenylene)[.

Part F

When the dibasic acid obtained in Part H is used in the procedure of Example 4, part C, the polymer obtained is poly[oxycarbonyl(1,4-phenylene)carbonylox-

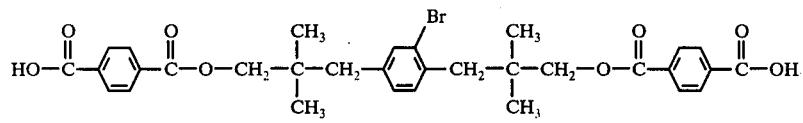

When α,α',2-tribromo-p-xylene [Hazlet et al., J. Org. Chem., 29, 2034-6 (1964)] is substituted for α,α'-dibromo-p-xylene in the procedure of Example 4, Part A, the diol obtained is 1,4-bis(3-hydroxy-2,2-dimethyly(2,2-dimethyl-1,3-propanediyl)(2-methyl-1,4-phenylene)(2,2-dimethyl-1,3-propandiyl)oxycarbonyl(1,4-phenylene)carbonyloxy(1,4-phenylene)].

Part J

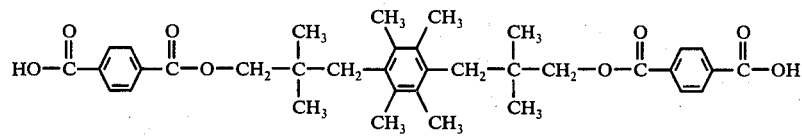

propyl)-2-bromobenzene, and the dibasic acid obtained in the procedure of Part B is 4,4'-[2-bromo-1,4-phenylenebis(2,2-dimethyl-3,1-propanediyl)(oxycarbonyl)]bis(benzoic acid).

Part G

The procedure of Example 4, Part A, was repeated except that 3,6-bis(chloromethyl)durene was substituted for α,α'-dibromo-p-xylene. The diol obtained was 1,4-bis(2,2-dimethyl-3-hydroxypropyl)tetramethylbenzene (m.p. = 147.5°-149° C, from methanol).

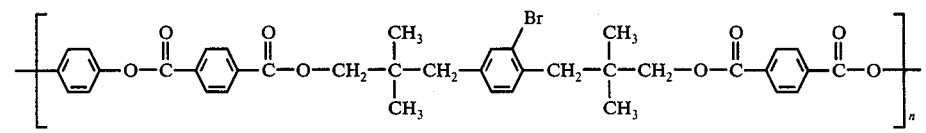

When the dibasic acid obtained in Part F is used in the procedure of Example 4, Part C, the polyester obtained is poly[oxycarbonyl(1,4-phenylene)carbonyloxy(2,2-dimethyl-1,3-propanediyl)(2-bromo-1,4-phenylene)(2,2-dimethyl-1,3-propanediyl)oxycarbonyl(1,4-phenylene)-carbonyloxy(1,4-phenylene)].

Part H

Anal. Calcd. for C₂₀H₃₄O₂: C, 78.38; H, 11.18: Found: C, 78.76; H, 11.24. 78.98 11.16

The infrared spectrum (KBr) contained an OH stretch band at 2.98 μ.

When this diol is substituted for 1,4-bis(3-hydroxy-2,2-dimethylpropyl)benzene in the procedure of Part B, the dibasic acid obtained is 4,4'-[2,3,5,6-tetramethyl-1,4-

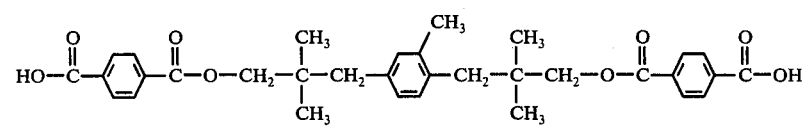

Similarly, when α,α'-dibromo-2-methyl-p-xylene is substituted for α,α'-dibromo-p-xylene in the procedure of Example 4, Part A, the intermediate diol obtained is 1,4-bis-(3-hydroxy-2,2-dimethylpropyl)-2-methylbenphenylenebis(2,2-dimethyl-3,1-propanediyl)-(oxycarbonyl)]bis(benzoic acid).

Part K

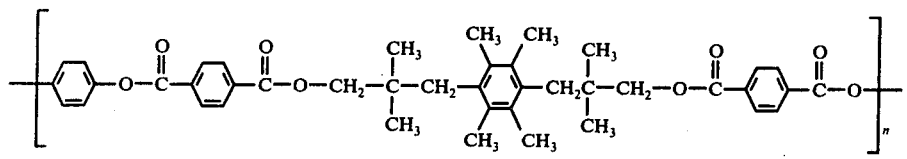

When the dibasic acid obtained in Part J is used in the procedure of Example 4, Part C, the ordered polyester obtained is poly[oxycarbonyl(1,4-phenylene)carbonyloxy(2,2-dimethyl-1,3-propanediyl)(2,3,5,6-tetramethyl-1,4-phenylene)-(2,2-dimethyl-1,3-propanediyl)oxycarbonyl(1,4-phenylene)-carbonyloxy(1,4-phenylene)].

Part L

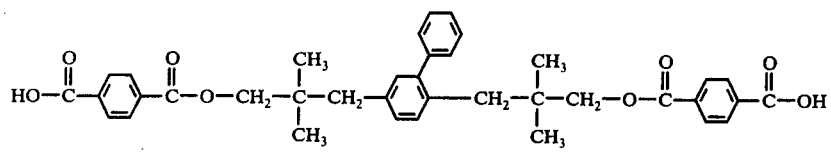

When 2,5-bis(bromomethyl)biphenyl ( U.S. Pat. No. 3,399,124) is substituted for α,α'-dibromo-p-xylene in the procedure of Example 4, Part A, the diol obtained is 2,5-bis(3-hydroxy-2,2-dimethylpropyl)biphenyl, and the dibasic acid obtained in the procedure of Part B is 4,4'-[1,1'-biphenyl-2,5-diylbis(2,2-dimethyl-3,1-propanediyl)(oxycarbonyl)]bis(benzoic acid).

Part M refluxed for 21½ hours and cooled to room temperature. Four grams of benzoyl peroxide was added and reflux was continued for 8 hours. The mixture was filtered hot and the solid was rinsed on the filter with 500 ml of hot carbon tetrachloride. Cooling the combined filtrate and rinsings gave 75.5 g of crude 3,3'-dichloro-4,4'-bis(bromomethyl)biphenyl melting at 148°–154° C. A recrystallization from chloroform raised the melting point to 159°–161° C.

Anal. Calcd. for $C_{14}H_{10}Cl_2Br_2$: C, 41.11; H, 2.47; Br, 39.08; Cl, 17.34. Found: C, 41.27; H, 2.68; Br, 38.62; Cl, 17.23. 41.1; H, 2.57; Br, 38.58; Cl, 17.26

The procedure of Example 4, Part A, was repeated except that the above material was substituted for α,α'-dibromo-p-xylene. The diol obtained was 3,3'-dichloro-4,4'-bis(3-hydroxy-2,2-dimethylpropyl)biphenyl) (m.p. 134.75°–135.75° C from chloroform).

Anal. Calcd. for $C_{22}H_{28}Cl_2O_2$: C, 66.83; H, 7.14; Cl, 17.94; Found: C, 66.86; H, 6.73; Cl, 17.40. C, 66.78; H, 7.01; Cl, 17.89

The infrared spectrum (KBr) contained an OH stretch band at 3.00 μ.

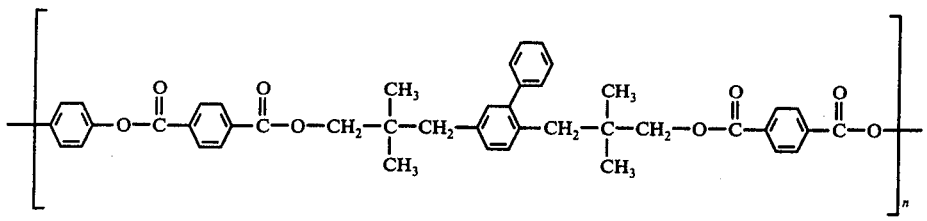

When the dibasic acid of Part L is used in the procedure of Example 4, Part C, the polyester obtained is poly[oxycarbonyl(1,4-phenylene)carbonyloxy(2,2-dimethyl-1,3-propanediyl)(1,1'-biphenyl)-2,5-diyl(2,2-dimethyl-1,3-propanediyl)oxycarbonyl(1,4-phenylene)-carbonyloxy(1,4-phenylene)].

Part N

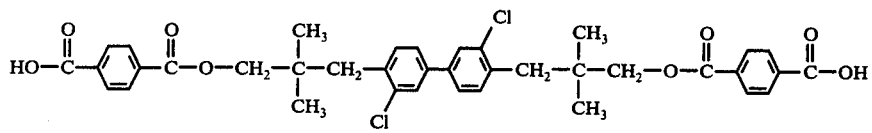

In a 2-liter flask equipped with a reflux condenser capped with a nitrogen bubbler was placed 83.7 g of 3,3'-dichloro-4,4'-bitolyl, 121.5 g of N-bromosuccinimide, 4.0 g of benzoyl peroxide, 630 ml of carbon tetrachloride, and a few boiling chips. The mixture was When this diol is substituted for 1,4-bis(3-hydroxy-2,2-dimethylpropyl)benzene in the procedure of Example 4, Part B, the dibasic acid obtained is 4,4'-[3,3'-dichloro-4,4'-biphenylenebis(2,2-dimethyl-3,1-propanediyl)-(oxycarbonyl)]bis(benzoic acid).

Part O

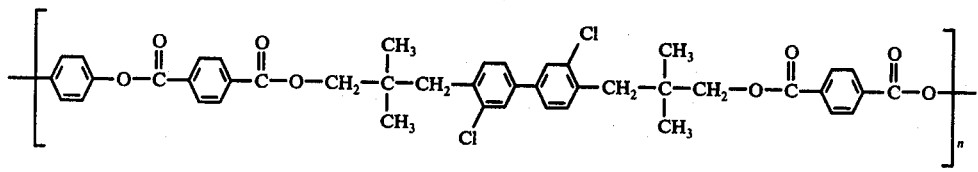

When the dibasic acid obtained in Part N is used in the procedure of Example 4, Part C, the ordered polyester obtained is poly[oxycarbonyl(1,4-phenylene)carbonyloxy(2,2-dimethyl-1,3-propanediyl)(3,3'-dichloro-1,1'-biphenyl)-4,4'-diyl(2,2-dimethyl-1,3-propanediyl)oxycarbonyl(1,4-phenylene)-carbonyloxy(1,4-phenylene)].

Part P

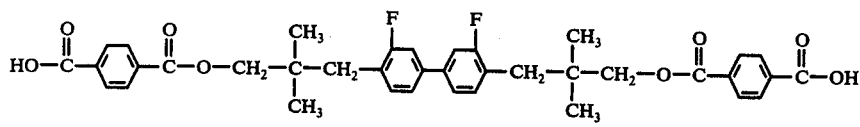

When 4,4'-bis(bromomethyl)-3,3'-difluorobiphenyl, prepared by coupling 2-fluoro-4-iodotoluene followed by bromination, is substituted for α,α'-dibromo-p-xylene in the procedure of Example 4, Part A, the diol obtained is 4,4'-bis(3-hydroxy-2,2-dimethylpropyl)-3,3'-difluorobiphenyl, and the dibasic acid obtained in the procedure of Part B is 4,4'-[3,3'-difluoro-1,1'-biphenyl-4,4'-diylbis(2,2-dimethyl-3,1-propanediyl)(oxycarbonyl)]bis(benzoic acid).

Part Q

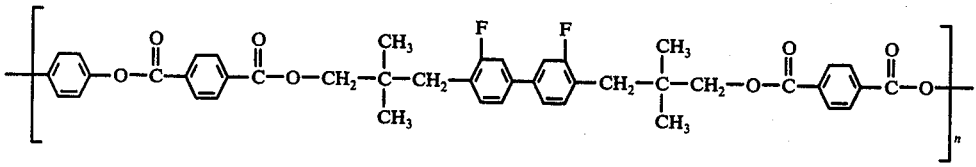

When the dibasic acid of Part P is used in the procedure of Example 4, Part C, the ordered polyester obtained is poly[oxycarbonyl(1,4-phenylene)carbonyloxy(2,2-dimethyl-1,3-propanediyl)(3,3'-difluoro-1,1'-biphenyl)-4,4'-diyl-(2,2-dimethyl-1,3-propanediyl)oxycarbonyl(1,4-phenylene)-carbonyloxy(1,4-phenylene)].

Part R

In a 1-liter flask equipped with a reflux condenser capped with a nitrogen T-tube was placed 41.0 g of 1-chloro-2,6-dimethylnaphthalene, 80 g of N-bromosuccinimide, 0.20 g of benzoyl peroxide, 475 ml of carbon tetrachloride and a few boiling chips. The mixture was refluxed for three hours and cooled to room temperature. After 0.30 g of α,α'-azobis(isobutyronitrile) was added, refluxing was continued for 17½ hours. After the mixture had been cooled to room temperature, it was filtered. The solid was rinsed on the filter with carbon tetrachloride and dried. Stirring of this solid with 500 ml of water for 2 hours, followed by filtration, rinsing of the solid on the filter with water, and drying, yielded 30.30 g of crude 1-chloro-2,6-bis(bromomethyl)naphthalene melting at 127°–129° C.

The filtrate from the first filtration was evaporated to 100 ml and refrigerated for several hours. Filtration of the resulting solid, rinsing on the filter with carbon tetrachloride, and drying yielded another 23.80 g of crude 1-chloro-2,6-bis(bromomethyl)naphthalene melting at 120°–128° C. Recrystallization of the combined products from chloroform raised the melting point to 131°–133° C.

Anal. Calcd. for $C_{12}H_9Br_2Cl$: C, 41.36; H, 2.60; Br, 45.87; Cl, 10.18. Found: C, 40.28; H, 2.51; Br, 46.96; Cl, 10.53. 40.22; H, 2.52; Br, 46.79; Cl, 10.52

The procedure of Example 4, Part A, was repeated except that the above material was substituted for α,α'-dibromo-p,p'-xylene. The diol obtained was 1-chloro-2,6-bis(3-hydroxy-2,2-dimethylpropyl)naphthalene (m.p. = 144°–145.5° C).

When this diol is substituted for 1,4-bis(3-hydroxy-

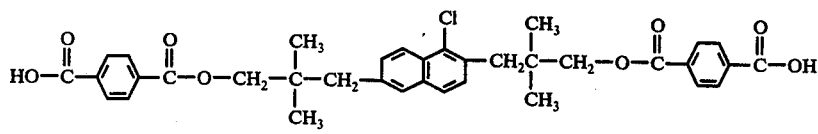

2,2-dimethylpropyl)benzene in the procedure of Part B, the dibasic acid obtained is 4,4'-[1-chloro-2,6-naphthalenebis(2,2-dimethyl-3,1-propanediyl)(oxycarbonyl)]bis(benzoic acid).

Part S

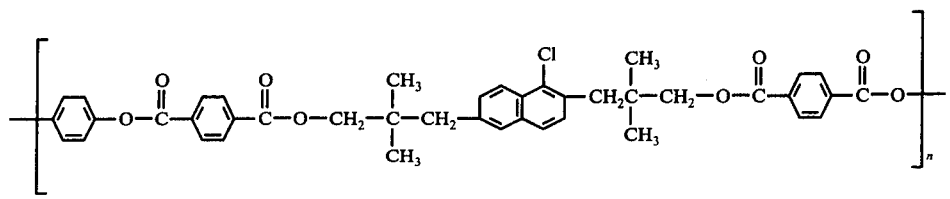

When the dibasic acid obtained in Part R is used in the procedure of Example 4, Part C, the ordered polyester obtained is poly[oxycarbonyl(1,4-phenylene)carbonyloxy(2,2-dimethyl-1,3-propanediyl)(1-chloro-2,6-naphthalene)diyl(2,2-dimethyl-1,3-propanediyl)oxycarbonyl(1,4-phenylene)carbonyloxy(1,4-phenylene)].

Part T

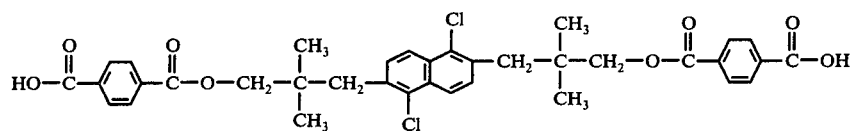

In a 250-ml flask equipped with a reflux condenser capped with a nitrogen T-tube was placed 12.10 g of 1,5-dichloro-2,6-dimethylnaphthalene, 20 g of N-bromosuccinimide, 0.10 g of benzoyl peroxide, 120 ml of carbon tetrachloride and a few boiling chips. The mixture was refluxed for 3 hours and cooled to room temperature. After 0.20 g of α,α'-azobis(isobutyronitrile) was added, refluxing was continued for 16½ hours. After the mixture had cooled to room temperature, the precipitated solid was filtered, rinsed on the filter with carbon tetrachloride and dried. Stirring of this solid for 2½ hours with 400 ml of water, followed by filtration and drying of the solid on the filter, gave 14.03 g of crude 1,5-dichloro-2,6-bis(bromomethyl)naphthalene melting at 219°–221° C. Recrystallization from refluxing toluene raised the melting point to 221°–222.5° C.

Anal. Calcd. for $C_{12}H_8Br_2Cl_2$: C, 37.64; H, 2.10; Br, 41.74; Cl, 18.52. Found: C, 38.11; H, 2,27; Br, 42.40; Cl, 18.04. C, 38.10; H, 2.21; Br, 42.24; Cl, 18.12

The procedure of Example 4, Part A, was repeated except that the above material was substituted for α,α'-dibromo-p,p'-xylene. The diol obtained was 1,5-dichloro-2,6-bis(3-hydroxy-2,2-dimethylpropyl)naphthalene (m.p. = 213¾°–214¾° C, from alcohol).

Anal. Calcd. for $C_{20}H_{26}Cl_2O_2$: C, 65.04; H, 7.10; Cl, 19.20. Found: C, 65.31; H, 7.14; Cl, 18.91. C, 64.85; H, 7.16; Cl, 18.99; C, 64.95; H; 7.28

The infrared spectrum (KBr) contained an OH stretch band at 3.00 μ.

When this diol is substituted for 1,4-bis(3-hydroxy-2,2-dimethylpropyl)benzene in the procedure of Example 4, Part B, the dibasic acid obtained is 4,4'-[1,5-dichloro-2,6-naphthalenebis(2,2-dimethyl-3,1-propanediyl)-(oxycarbonyl)]bis(benzoic acid).

Part U

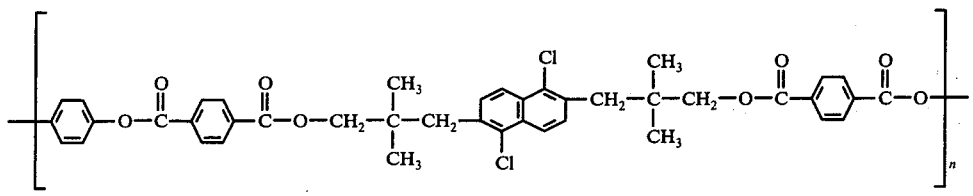

When the dibasic acid obtained in Part T is used in the procedure of Example 4, Part C, the ordered polyester obtained is poly[oxycarbonyl(1,4-phenylene)carbonyloxy(2,2-dimethyl-1,3-propanediyl)(1,5-dichloro-2,6-naphthalene)diyl(2,2-dimethyl-1,3-propanediyl)oxycarbonyl(1,4-phenylene)-carbonyloxy(1,4-phenylene)].

EXAMPLE 5

Part A

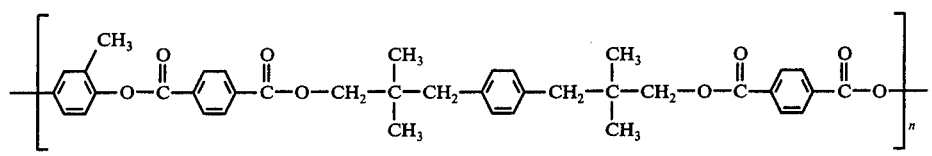

To a glass reactor with a nitrogen bleed and a sidearm was added 21.00 g (0.0525 M) of the diacid from Example 4, Part C, and 11.193 g (0.0538 M) of methylhydroquinone diacetate. The resulting mixture was heated as in Example 2, Part A. The resulting poly[oxycarbonyl(1,4-phenylene)carbonyloxy(2,2-dimethyl-1,3-propanediyl)(1,4-phenylene)(2,2-dimethyl-1,3-propanediyl)oxycarbonyl(1,4-phenylene)carbonyloxy(2-methyl-1,4-phenylene)] had a PMT of approximately 400° C, an inherent viscosity of 0.62 and showed low crystallinity by X-ray diffraction.

Part B

Polymer from Part A was spun at a spinneret temperature of 370° C and the fiber was wound up at 250 yd/min. The fiber could not be drawn and after being heated at 250° C for 18 hours under a nitrogen atmosphere, had an orientation angle of 21°, was of medium crystallinity, had a T/E/Mi at room temperature of 6.5/2.1/302 and a T/E/Mi at 150° C of 5.2/2/240.

EXAMPLE 6

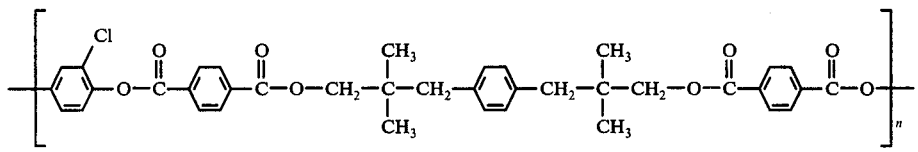

To a glass reactor with a nitrogen bleed and a sidearm was added 2.550 g (0.005 M) of the diacid from Part C of Example 4 and 1.211 g (0.0053 M) of chlorohydroquinone diacetate. The resulting mixture was heated under a nitrogen atmosphere for 18 hours at 242° C, for 2 hours at 275° C, and for 2 hours at 305° C, followed by 2 hours at 305° C at 0.01 mm. The resulting poly[oxycarbonyl(1,4-phenylene)carbonyloxy(2,2-dimethyl-1,3-propanediyl)(1,4-phenylene(2,2-dimethyl-1,3-propanediyl)oxycarbonyl(1,4-phenylene)carbonyloxy(2-chloro-1,4-phenylene)] had a PMT >400° C and was insoluble in a 40/60 weight mixture of 1,1,2,2-tetrachloroethane and phenol.

All the polymers in the preceding Examples had values of *n* in excess of 10.

I claim:

1. Thermally stable, rigid, dibasic acids of the formula

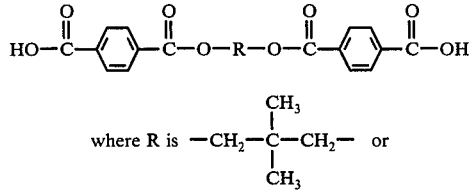

where R is —CH$_2$—C(CH$_3$)$_2$—CH$_2$— or

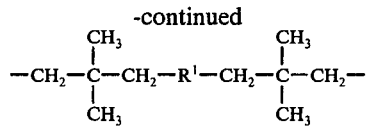

where R$^1$ is an arylene selected from the group consisting of 1,4-phenylenes, 4,4'-biphenylenes and 2,6-naphthylenes, said arylene being unsubstituted or substituted with halo, lower alkyl or phenyl.

2. The dibasic acid of claim 1 of the formula

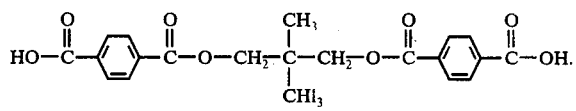

3. The dibasic acids of claim 1 of the formula

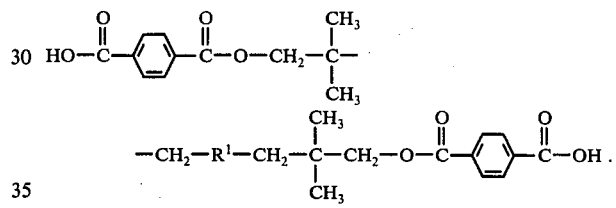

4. The dibasic acid of claim 3 of the formula

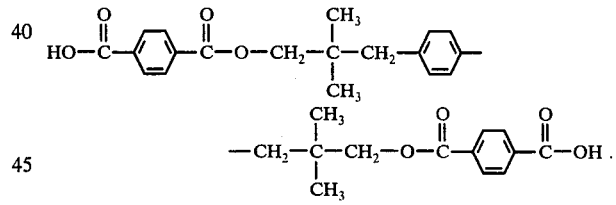

* * * * *